United States Patent [19]
Friedman et al.

[11] Patent Number: 5,372,931
[45] Date of Patent: Dec. 13, 1994

[54] USE OF 4'-HYDROXY- AND 4'-ALKOXY-SUBSTITUTED ELECTRON TRANSFER AGENTS IN COMPOSITIONS, ELEMENTS, TEST KITS AND ANALYTICAL METHODS

[75] Inventors: Alan E. Friedman; Thomas R. Kissel, both of Rochester, N.Y.

[73] Assignee: Eastman Kodak Compay, Rochester, N.Y.

[21] Appl. No.: 995,479

[22] Filed: Dec. 22, 1992

[51] Int. Cl.$^5$ .................. C12Q 1/68; G01N 33/543; C09K 11/00
[52] U.S. Cl. ........................ 435/6; 435/7.4; 435/7.9; 435/7.92; 435/7.93; 435/7.94; 435/7.95; 435/28; 435/970; 252/700; 422/56; 422/57
[58] Field of Search .................. 292/700; 435/6, 7.9, 435/7.92, 7.93, 7.94, 7.95, 28, 962, 963, 967, 968, 7.4; 422/56, 57

[56] References Cited

U.S. PATENT DOCUMENTS

| | | | |
|---|---|---|---|
| 3,492,349 | 1/1970 | Doyle et al. | 564/223 |
| 3,651,141 | 3/1972 | Galantay | 564/158 |
| 3,746,741 | 7/1973 | Hubele | 560/34 |
| 4,265,909 | 5/1981 | Jollow et al. | 514/629 |
| 4,288,592 | 9/1981 | Rauhut et al. | 544/159 |
| 4,424,150 | 1/1984 | Khanna | 530/300 |
| 4,504,413 | 3/1985 | Khanna | 435/188 |
| 4,524,217 | 6/1985 | Davenport | 564/223 |
| 4,598,044 | 7/1986 | Kricka et al. | 435/28 |
| 4,605,754 | 8/1986 | Khanna | 560/19 |
| 4,746,607 | 5/1988 | Mura et al. | 435/25 |
| 4,828,983 | 5/1989 | McClune | 435/7 |
| 4,973,752 | 11/1990 | Fruchey | 564/223 |
| 4,999,457 | 3/1991 | Fruchey | 564/223 |
| 5,024,935 | 6/1991 | McClune et al. | 435/7.1 |
| 5,047,318 | 9/1991 | Snyder et al. | 435/5 |
| 5,051,356 | 9/1991 | Warren et al. | 435/7.34 |

FOREIGN PATENT DOCUMENTS

| | | | |
|---|---|---|---|
| 299891 | 7/1987 | European Pat. Off. | C07C 37/62 |
| 455471 | 4/1991 | European Pat. Off. | C07D 277/24 |
| 02062853 | 8/1988 | Japan | C07C 233/15 |
| 625783 | 9/1976 | Switzerland | A01N 37/22 |

OTHER PUBLICATIONS

Daly et al, *Biochem. Pharm.*, 17, pp. 31–36 (1968).
Calder et al, *Aust. J. Chem.*, 29, pp. 1801–1808 (1976).
Calder et al, *Chem.-Biol. Interactions*, 8, pp. 87–90 (1974).

*Primary Examiner*—Esther M. Kepplinger
*Assistant Examiner*—Lora M. Green
*Attorney, Agent, or Firm*—J. Lanny Tucker

[57] ABSTRACT

Aqueous compositions, test kits, test devices and methods can be used to detect hydrogen peroxide or peroxidase by generating a colorimetric or chemiluminescent signal in the presence of the analyte. Signal generation is enhanced by the presence of certain substituted 4-hydroxy- or 4-alkoxy-substituted phenyl or naphthyl electron transfer agents.

24 Claims, 5 Drawing Sheets

USE OF 4'-HYDROXY- AND 4'-ALKOXY-SUBSTITUTED ELECTRON TRANSFER AGENTS IN COMPOSITIONS, ELEMENTS, TEST KITS AND ANALYTICAL METHODS

FIELD OF THE INVENTION

This invention relates to compositions, analytical elements, test kits and methods which utilize certain 4'-hydroxy- and alkoxy-substituted anilides as electron transfer agents. In particular, such compounds are useful to improve sensitivity in analytical and diagnostic methods.

BACKGROUND OF THE INVENTION

It is well known to perform a quantitative or qualitative analysis of an aqueous liquid by contacting that liquid with a combination of reagents capable of yielding a detectable product in proportion to the concentration of the analyte in the liquid. One type of useful assay utilizes enzymatic reactions wherein the analyte, upon contact with the appropriate reagents, reacts with oxygen in the presence of a suitable enzyme to produce hydrogen peroxide in proportion to concentration of the analyte. A detectable product is then produced by the reaction of hydrogen peroxide in proportion to the concentration of the analyte in the test liquid. Peroxidase is generally used in such assays.

In other assays, a peroxidase is reacted in the presence of hydrogen peroxide which has been added to the system to measure the amount of a particular analyte. Analytes such as glucose, triglycerides, uric acid, cholesterol and creatine kinase can be so detected as well as specific binding ligands in specific binding assays wherein the peroxidase is used as a detectable label. Such determinations can be carried out in solution, dry analytical assays or diagnostic test devices. The signals produced in such assays can be a colorimetric, chemiluminescent or fluorescent signal using well known signal generating reagents.

It has been previously demonstrated that certain phenols and anilines can be used to enhance the production of a colorimetric signal using peroxidase as a reagent in signal generation. See, for example, U.S. Pat. No. 4,828,983 (McClune).

There are also several major types of luminescent or luminometric assays which produce an emission of light as a result of the presence of the analyte of interest. These assays are also known as chemiluminescent assays and are described, for example, in U.S. Pat. No. 4,729,950 (Kricka et al) and publications noted therein. Various aromatic amines and phenols, such as p-iodophenol, are considered useful for enhancing the production of light in such assays (see also U.S. Pat. No. 4,598,044 of Kricka et al).

One preferred enhancer of colorimetric assays has been 4'-hydroxyacetanilide, which is described in the McClune patent noted above.

Although 4'-hydroxyacetanilide shows remarkable behavior in many analytical systems, there is a need for further improvement. For example, high concentrations of 4'-hydroxyacetanilide do not produce correspondingly high signal generation. In addition, the stability of the compound needs to be increased.

SUMMARY OF THE INVENTION

The need for further improvement in analytical compositions and methods has been met with a composition for providing a colorimetric or chemiluminescent signal having a pH of from about 5 to about 10, and comprising:

a) a colorimetric or chemiluminescent signal generating reagent which provides a signal in response to the catalytic activity of peroxidase, the signal generating reagent being selected from the group consisting of:
a 2,3-dihydro-1,4-phthalazinedione derivative,
a tetrazolium salt,
a diazonium salt, and
an imidazole or triarylmethane leuco dye, and b) an electron transfer agent having structure (I):

structure (I):

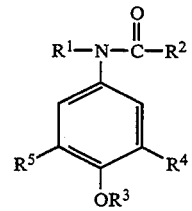

structure (II):

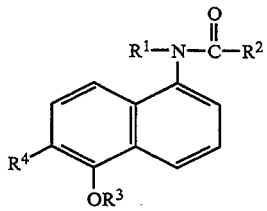

structure (III):

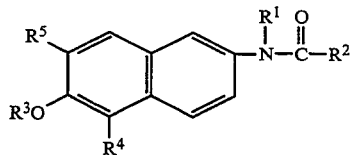

or structure (IV):

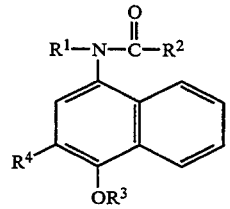

wherein $R^1$ is hydrogen or alkyl of 1 to 4 carbon atoms,
$R^2$ is hydrogen, alkyl of 1 to 4 carbon atoms, hydroxyalkyl of 1 to 4 carbon atoms, alkoxyalkyl of 1 to 4 carbon atoms, aminoalkyl of 1 to 4 carbon atoms, halogenated alkyl of 1 to 4 carbon atoms, or alkenyl of 2 to 5 carbon atoms,
$R^3$ is hydrogen or alkyl of 1 to 4 carbon atoms, and
$R^4$ and $R^5$ are independently hydrogen or an electron withdrawing group having a Hammett sigma value of at least about 0.01, provided that in structure (I), at least one of $R^4$ and $R^5$ is an electron withdrawing group having a Hammett sigma value of at least about 0.01.

Further, an aqueous composition which is buffered to a pH of from about 5 to about 10 comprises a peroxidase or peroxidase-labeled specific binding molecule, and an electron transfer agent as defined above.

This invention also provides a diagnostic test kit for the determination of an analyte as the result of the catalytic activity of peroxidase, the kit comprising, in individual packaging:
  i) the composition described above, and
  ii) peroxidase or a peroxidase-labeled specific binding molecule.

A test device for the detection of peroxidase or an analyte catalytically related to peroxidase comprises an absorbent carrier material, and contains a colorimetric or chemiluminescent signal generating reagent and an electron transfer agent having structure (I), (II), (III) or (IV) as described above.

Another embodiment of this invention is a method for producing a detectable signal in response to peroxidase comprising:
  A. reacting a peroxidase in the presence of
    a) the signal generating reagent described above,
    b) an electron transfer agent having structure (I), (II), (III) or (IV) as described above, and
    c) an oxidant, to produce a detectable colorimetric or chemiluminescent signal, and
  B. determining the resulting colorimetric or chemiluminescent signal as a measure of peroxidase. A specific binding assay for the determination of a specific binding ligand comprises:
  A. complexing a specific binding ligand with a receptor specific for the ligand to form a specific binding complex,
  B. labeling the specific binding complex with a peroxidase which is either conjugated with the receptor, or is conjugated with a specific binding molecule which is specifically reactive with either the specific binding ligand or the receptor,
  C. after separating uncomplexed materials from the peroxidase-labeled complex, contacting the peroxidase-labeled complex with:
    a) the colorimetric or chemiluminescent signal generating reagent described above,
    b) an electron transfer agent having structure (I), (II), (III) or (IV) as described above, and
    c) an oxidant, to produce a detectable colorimetric or chemiluminescent signal, and
  D. determining the resulting signal as a measure of the specific binding ligand.

The present invention provides all of the known advantages associated with the use of various colorimetric or chemiluminescent assays utilizing peroxidase in the reaction scheme. However, by using the noted electron transfer agents defined by structures (I), (II), (III) and (IV), the assays are more sensitive.

Moreover, the present invention demonstrates stable kinetics, especially for the chemiluminescent assays described herein, wherein the emitted light signal remains at a constant intensity for a longer period of time.

DETAILED DESCRIPTION OF THE INVENTION

Figure 1:
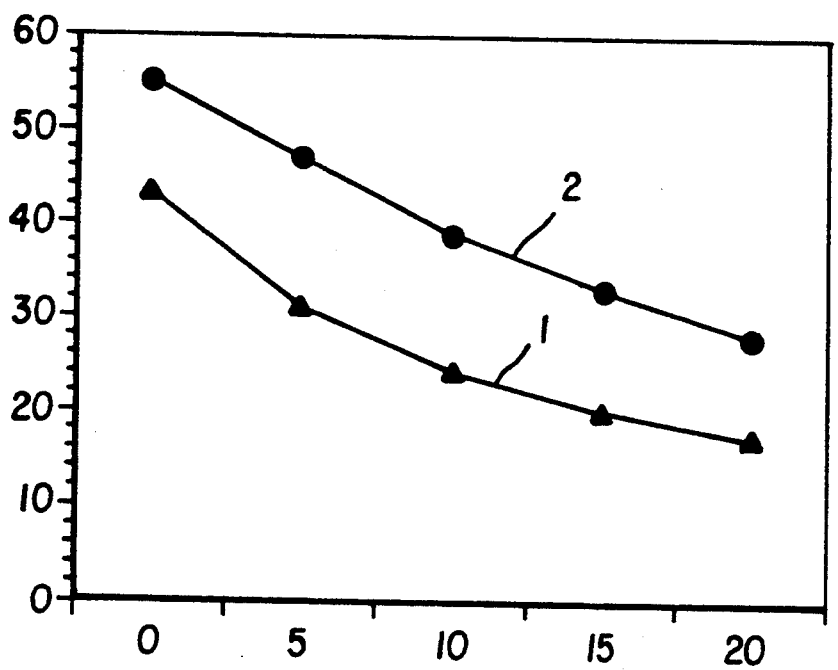
FIG. 1 is a graphical representation of chemiluminescent signal obtained using a composition of this invention and a Control composition, as described in Example 4 below.

The present invention can be practiced to advantage in any analytical method designed to generate a colorimetric or chemiluminescent signal in response to the presence of a peroxidase. Such assays can involve the detection of an organic or inorganic peroxide (such as hydrogen peroxide) or peroxidase (in its free form), or the detection of a non-immunological analyte other than peroxidase or hydrogen peroxide. In particular, the invention is useful in the practice of specific binding assays which generate a colorimetric, chemiluminescent or fluorescent signal.

The assay can be qualitative or quantitative or both, and be used to detect a biological or chemical substance (that is, an analyte) in aqueous liquids, including human or animal biological fluids, waste fluids, foods, environmental effluent, chemical processing liquids and other specimens readily apparent to one skilled in the art.

Hydrogen peroxide (or another peroxide) can be determined with this invention. In addition, the invention can be used to determine analytes which are capable of producing hydrogen peroxide, that is the analyte participates in one or more reactions which produce hydrogen peroxide in the presence of suitable signal generating reagents and a peroxidase. Such analytes are considered herein as "analytes catalytically related to peroxidase".

In a preferred embodiment, the invention is useful for the determination of a specific binding ligand, or its corresponding receptor (that is, a substance which specifically binds with the ligand). Such ligands include, but are not limited to, antibodies and other proteins (including lipoproteins, blood proteins, enzymes and glycoproteins), haptens, drugs, hormones, steroids, toxins, viruses, bacteria, vitamins, saccharides (including polysaccharides), lipids, nucleic acids, nonproteinaceous blood components, or any components thereof readily understood by one skilled in the art.

A preferred chemiluminescent signal generating reagent is a 2,3-dihydro-1,4-phthalazinedione derivative (identified herein as "DPD"). Any free or conjugated 2,3-dihydro-1,4-phthalazinedione derivative that can be converted to an excited state in a chemiluminescent reaction and then returns to a non-excited state with the emission of light, is useful in the practice of this invention. A considerable number of such compounds are known in the art, including those described in U.S. Pat. No. 4,598,044 and *Chemiluminescence in Organic Chemistry*, Gundermann and McCapra, Springer-Verlag, Berlin, 1987, pages 204–207. Such compounds are generally known as "luminol type hydrazides" and include phthalic hydrazides, naphthalene-1,2-dicarboxylic acid hydrazides, anthracene-2,3-dicarboxylic acid hydrazides, phenathrene-1,2-dicarboxylic acid hydrazides, fluorene-1,2-dicarboxylic acid hydrazides, benzo[g,h,i]-perylene-1,2-dicarboxylic acid hydrazides, coronene-1,2-dicarboxylic acid hydrazides, and others readily apparent to one skilled in the art.

In particular, the DPD is defined by the structure (V):

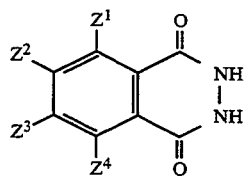

wherein $Z^1$, $Z^2$, $Z^3$ and $Z^4$ are independently hydrogen, alkyl of 1 to 6 carbon atoms (such as methyl, ethyl, isopropyl, t-butyl, sec-pentyl and hexyl), alkenyl of 2 to 6 carbon atoms [such as ethenyl, 1-propenyl, isobutenyl, 2-(N,N-diisopropylamino)vinyl, 2-(N,N-diisobutylamino)vinyl, 2-(N,N-diisopentylamino)vinyl and 2-hexenyl], hydroxy, alkoxy of 1 to 6 carbon atoms (such as methoxy, ethoxy, isopropoxy, t-butoxy and hexoxy), carboxy, amino [including amino substituted with alkyl or alkanoyl, such as methylamino, ethylamino, amido (for example, acetamido and hexanamido), dimethylamino, diethylamino and diisobutylamino], conjugated aminoalkenyl (for example, as defined below) or aminoaryl [including substituted aminoaryl, such as p-(N,N-dimethylamino)phenyl, e,uns/p/ -(N,N-diethylamino)phenyl and 5-amino-2,3-dihydro-1,4-phthalazinedion-8-yl (also known as luminyl)].

At least one of $Z^1$ and $Z^2$ is amino (including substituted amino, as defined above), conjugated aminoalkenyl (including substituted aminoalkenyl as described above) or aminoaryl [such as p-(N,N-dimethylamino)phenyl, p-(N,N-diethylamino)phenyl and 5-amino-2,3-dihydro-1,4-phthalazinedion-8yl]. As used herein, "conjugated aminoalkenyl" refers to a monovalent group capable of electron resonance from the amino group through the alkenyl group to the aromatic ring of the phthalazinedione where it is substituted, and includes for example, a dialkylaminovinyl group [such as 2-(N,N-diisopropylamino)vinyl, 2-(N,N-diisobutylamino)vinyl and 2-(N,N-diisopentylamino)vinyl], and dialkylaminobutadienyl groups, such as 4-(N,N-diethylamino)-1,3-butadien-1-yl.

Alternatively, any adjacent two, adjacent three or all of $Z^1$, $Z^2$, $Z^3$ and $Z^4$ (that is, combinations of two or three adjacent groups, or all four groups) can be taken together to form a fused ring system containing one or more aromatic rings. Such fused rings can be substituted with one or more hydroxy, amino (substituted or unsubstituted as described above) or alkoxy of 1 to 4 carbon atoms (such as methoxy, ethoxy and isopropoxy). Preferably, such fused rings are substituted with one or more primary, secondary or tertiary amines, hydroxy or alkoxy as described above.

Representative useful DPD compounds include, but are not limited to, luminol, isoluminol, N-(4-aminobutyl)-N-ethylisoluminol hemisuccinimide, N-(6-aminohexyl)-N-ethylisoluminol, N-ethylisoluminol and 7-dimethylaminonaphthalene-1,2-dicarboxylic acid hydrazide. Luminol (5-amino-2,3-dihydro-1,4-phthalazinedione) and isoluminol (6-amino-2,3-dihydro-1,4-phthalazinedione) are preferred, and luminol is most preferred.

Other useful classes of DPD compounds are described in the Gundermann and McCapra publication noted above, and include substituted or unsubstituted phthalic acid hydrazides, anthracene-2,3-dicarboxylic acid hydrazides, phenathrene dicarboxylic acid hydrazides, fluorene-1,2-dicarboxylic acid hydrazides, benzo [g,h,i]perylene-1,2-dicarboxylic acid hydrazides and coronene-1,2-dicarboxylic acid hydrazides, such as those illustrated by the following structures:

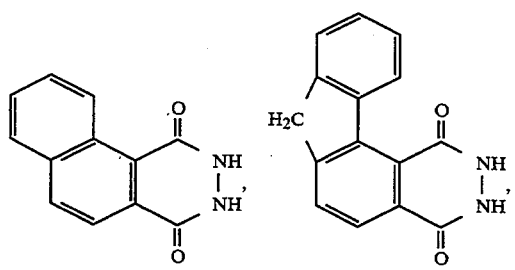

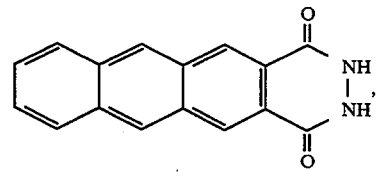

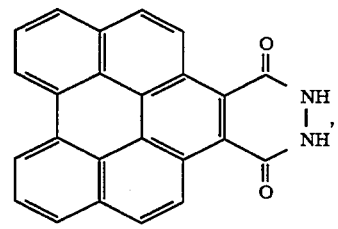

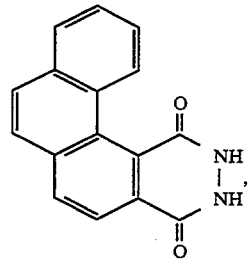

and

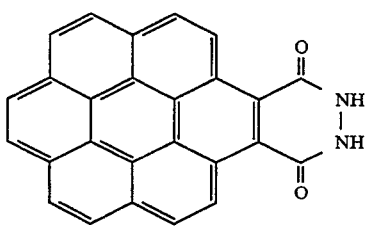

The DPD compounds noted above can be obtained commercially, or be prepared using conventional starting materials and known procedures.

Other useful signal generating reagents include imidazole or triarylmethane leuco dyes, such as those described in U.S. Pat. No. 4,089,747 (Bruschi) and references noted therein, EP-A-0 122 641 (published Oct. 24, 1984), Japanese Patent Publication No. 58(1983)-045557 and U.S. Pat. No. 4,670,385 (Babb et al).

The triarylimidazole leuco dyes described in the Bruschi patent are preferred for generating a colorimetric signal in the practice of this invention. Such leuco dyes generally have the structure (VI):

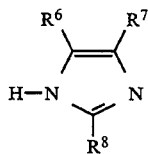

wherein $R^6$, $R^7$ and $R^8$ are independently an organic group such that at least one of them is an o- or p-hydroxysubstituted aryl group of up to 18 carbon atoms in the aromatic ring, and the other two groups being aryl groups chosen such that the imidazole oxidation potential is within the range of from about −70 to about +100 mV as measured by cyclic voltammetry against a standard calomel electrode using a carbon based electrode. Oxidation potential measurements can be made according to conventional electrochemical techniques (see for example, Sawyer et al, *Experimental Electrochemistry for Chemists*, John Wiley & Sons, New York, 1974).

As used in the definition of the leuco dyes, "aryl" is meant to include aromatic hydrocarbon groups such as phenyl, naphthyl or anthryl, tolyl, xylyl and other substituted aromatic groups. The number of carbon atoms refers to the total nuclear carbon atoms as well as those in the substituents. At least one of the $R^6$, $R^7$ and $R^8$ groups has an ortho or para electron donating substituent such as an alkyoxy (—OR') wherein R' is alkyl of 1 to 8 carbon atoms (such as methyl, ethyl, isopropyl, t-butyl, hexyl, chloromethyl or methoxymethyl), or a dialkylamino wherein alkyl is as just defined. Useful leuco dyes can be purchased from commercial sources or prepared using known technology.

Particularly useful triarylimidazole leuco dyes are:
2-(4-hydroxy-3,5-dimethoxylphenyl)-4,5-bis(4methoxyphenyl)imidazole,
2-(3,5-dibromo-4-hydroxyphenyl)-4,5-diphenylimidazole,
3-(3-bromo-5-methoxy-4-hydroxyphenyl)-4,5-bis(4methoxyphenyl)imidazole,
4,5-bis(4-dimethylaminophenyl)-2-(4-hydroxyphenyl)imidazole,
4,5-bis(4-dimethylaminophenyl)-2-(4-hydroxy-3-methoxyphenyl)imidazole, and
2-(4-hydroxyphenyl)-4,5-bis(4-methoxyphenyl)imidazole.

The leuco dyes described above can be prepared using known materials and procedures, and some are available commercially.

The diazonium and tetrazolium salts useful in the practice of this invention must be those capable of reacting in the presence of peroxidase and an oxidant to produce a chromophore. A diazonium salt is generally an organic salt of a compound having a diazonium radical.

Particularly useful diazonium salts include, but are not limited to, those having the following structure (VII):

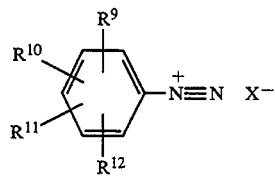

wherein $R^9$, $R^{10}$, $R^{11}$ and $R^{12}$ are independently hydrogen, halo (such as chloro, bromo or iodo), alkyl of 1 to 12 carbon atoms (such as methyl, ethyl, isopropyl, t-butyl, sec-butyl, n-butyl, pentyl, octyl, isononyl and dodecyl), nitro, cyano, alkoxy of 1 to 6 carbon atoms (such as methoxy, ethoxy, pentoxy, isopropoxy, e,uns/t/ -butoxy and hexoxy), aryloxy of 6 to 10 carbon atoms in the aromatic ring, including aryloxy substituted with alkoxy and alkyl as defined above (such as phenoxy, naphthoxy, tolyloxy and p-nitrophenoxy), aryl of 6 to 10 carbon atoms (such as phenyl, naphthyl, p-methylphenyl, m-ethoxyphenyl, p-cyanophenyl and o-methoxyphenyl), acyl of 1 to 12 carbon atoms ( such as acetyl, propionyl, benzoyl and butyryl), and substituted or unsubstituted carbamoyl or sulfamoyl (such as carbamoyl, sulfamoyl, N,N-dimethylcarbamoyl and N,N-diethylsulfamoyl). Preferably, $R^9$, $R^{10}$, $R^{11}$ and $R^{12}$ are independently hydrogen, methyl, chloro, N,N-diethylsulfamoyl, nitro or methoxy.

In addition, any two of these radicals at adjacent positions on the ring can be taken together to represent a 6- to 10-membered fused aromatic ring system, including both heterocyclic or carbocyclic fused aromatic rings. Such rings can include carbon, nitrogen, oxygen or sulfur atoms in the ring structure. Preferably, 6- to 10-membered carbocyclic ring systems are formed in this manner.

In the salt noted above, $X^-$ represents any suitable anion which does not inhibit or act as a substrate for peroxidases, such as halide (for example, chloride, bromide and fluoride), tetrafluoroborate, nitrate, perchlorate, ptoluenesulfonate and others readily apparent to one skilled in the art.

Representative useful diazonium salts include, but are not limited to, N',N'-diethyl-4-methoxymetanilamide diazonium salt (known as Fast Red-ITR salt), 4-chloro-2-methylbenzendiazonium salt (known as Fast Red TR salt), diazotized 2-methoxy-5-chloroaniline (known as Fast Red RC salt) and diazotized 5-nitro-2-amino-1-methoxybenzene (known as Fast Red B).

Tetrazolium salts are organic salts in which the organic portion contains one or two tetrazole rings, generally with aryl substituents at various positions. Tetrazolium salts having two tetrazole rings can be formed to provide a biphenyl nucleus with a tetrazole ring in each of the 4- and 4'- positions of the biphenyl nucleus.

Many useful diazonium and tetrazolium compounds are described for example, in U.S. Pat. No. 3,905,872 (Forgione), U.S. Pat. No. 4,772,553 (Fujii et al), U.S. Pat. No. 4,892,817 (Pawlak) and U.S. Pat. No. 4,892,833 (Weiss et al) and Japanese Publication 63/088,000 (published Apr. 19, 1988). Many diazonium and tetrazolium salts useful herein are available from a number of commercial sources, and those not readily available can be readily prepared by a skilled organic chemist using available reagents and known procedures.

A second critical component of the signal-providing composition of this invention is an electron transfer agent having any of structures (I):

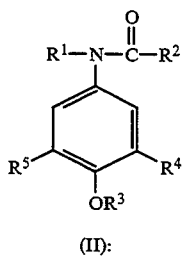

(II):

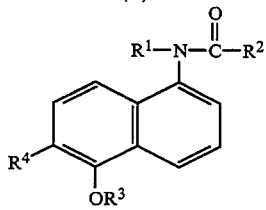

(III):

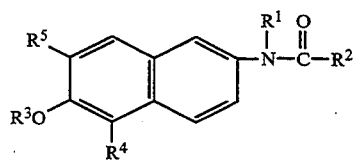

or (IV):

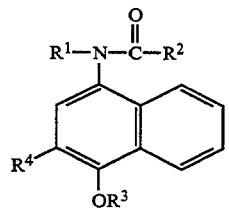

wherein $R^1$ is hydrogen or alkyl of 1 to 4 carbon atoms ( such as methyl, ethyl, isopropyl, hydroxymethyl, aminomethyl and methoxymethyl). Preferably, $R^1$ is hydrogen.

In structure (I), (II), (III) and (IV), $R^2$ is hydrogen, alkyl of 1 to 4 carbon atoms (such as methyl, ethyl, isopropyl, e,uns/t/ -butyl and isobutyl), alkoxyalkyl of 1 to 4 carbon atoms (such as methoxymethyl and methoxyethyl), hydroxyalkyl of 1 to 4 carbon atoms (such as hydroxymethyl, 1-hydroxyethyl, 2-hydroxyethyl and 2,3-dihydroxypropyl), aminoalkyl of 1 to 4 carbon atoms (such as aminomethyl, 2-aminoethyl, 3-aminopropyl, 2,4-diaminobutyl, methylaminomethyl, 2,2-dimethylaminoethyl and 4-aminobutyl), haloalkyl of 1 to 4 carbon atoms (such as chloromethyl, bromomethyl, 2-chloroethyl, 1,1-dichloromethyl, 1,1,1-trichloromethyl, 2,2,2-trichloroethyl and 3-chloropropyl), or alkenyl of 2 to 5 carbon atoms (such as ethenyl, 1-propenyl, isopropenyl and 2-butenyl). Preferably, $R^2$ is hydrogen, methyl or ethenyl.

$R^3$ is hydrogen or alkyl of 1 to 4 carbon atoms (such as methyl, ethyl, isopropyl, t-butyl, n-butyl and isobutyl). Preferably, $R^3$ is hydrogen or methyl.

$R^4$ and $R^5$ are independently hydrogen or an electron withdrawing group having a Hammett sigma value of at least about 0.01, and preferably at least about 0.3. Hammett sigma values are calculated in accordance with standard procedures described, for example, in *Steric Effects in Organic Chemistry*, John Wiley & Sons, Inc., 1956, pp. 570-574 and *Progress in Physical Organic Chemistry*, Vol. 2, Interscience Publishers, 1964, pp. 333-339. Representative electron withdrawing groups having positive Hammett sigma values include cyano, carboxy, nitro, halo (fluoro, bromo, chloro or iodo), trihalomethyl (for example, trifluoromethyl or trichloromethyl), carbonyl, carbamoyl, sulfonyl, sulfamoyl, esters, and others readily apparent to one skilled in the art. Preferred electron withdrawing groups are halo (such as chloro or bromo) and cyano. Chloro and cyano are more preferred electron withdrawing groups, and chloro is most preferred for either of $R^4$ and $R^5$.

In the foregoing structure (I), at least one of $R^4$ and $R^5$ must be an electron withdrawing group as defined above. In foregoing structures (II), (III) and (IV), at least one of $R^4$ and $R^5$ can be an electron withdrawing group, but this is not required.

Representative electron transfer agents having structure (I) include:
3'-chloro-4'-hydroxyacetanilide,
3',5'-dichloro-4'-hydroxyacetanilide,
3'-fluoro-4'-hydroxyacetanilide,
3',5'-difluoro-4'-hydroxyacetanilide,
3'-bromo-4'-hydroxyacetanilide,
3',5'-dibromo-4'-hydroxyacetanilide,
3'-cyano-4'-hydroxyacetanilide,
3',5'-dicyano-4'-hydroxyacetanilide,
N-methyl-N-(3-chloro-4-hydroxyphenyl)acetamide,
N-(3-chloro-4-hydroxyphenyl)methacrylamide,
N-(3-chloro-4-methoxyphenyl)acetamide,
N-(3-chloro-4-hydroxyphenyl)-2-chloroacetamide,
N-(3-chloro-4-hydroxyphenyl)-2,2-dichloroacetamide,
N-(3-chloro-4-hydroxyphenyl)-2,2,2-trichloroacetamide,
N-(3-chloro-4-hydroxyphenyl)-2-hydroxyacetamide,
N-(3-chloro-4-hydroxyphenyl)-2-methoxyacetamide, and
N-(3-chloro-4-hydroxyphenyl)-2-aminoacetamide.

Representative electron transfer agents of structure (II) include:
N-(5-hydroxy-1-naphthyl)acetamide,
N-(5-hydroxy-6-fluoro-1-naphthyl)acetamide,
N-(5-hydroxy-6-chloro-1-naphthyl)acetamide,
N-(5-hydroxy-6-cyano-1-naphthyl)acetamide,
N-methyl-N-(5-hydroxy-1-naphthyl)acetamide,
N-methyl-N-(5-hydroxy-6-chloro-1-naphthyl)acetamide,
N-(5-methoxy-1-naphthyl)acetamide,
N-(5-methoxy-6-chloro-1-naphthyl)acetamide,
5N-(5-hydroxy-1-naphthyl) -2-chloroacetamide,
N-(5-hydroxy-1-naphthyl)-2,2-dichloroacetamide, N-(5-hydroxy-6-chloro-1-naphthyl)-2,2-dichloroacetamide,
N-(5-hydroxy-1-naphthyl)-2,2,2-trichloroacetamide,
N-(5-hydroxy-6-chloro-1-naphthyl)-2,2,2-trichloroacetamide,
N-(5-hydroxy-1-naphthyl)-2-hydroxyacetamide,
N-(5-hydroxy-6-chloro-1-naphthyl)-2-hydroxyacetamide,
N-(5-hydroxy-1-naphthyl)-2-methoxyacetamide,
N-(5-hydroxy-6-chloro-1-naphthyl)-2-methoxyacetamide,
N-(5-hydroxy-1-naphthyl)-2-aminoacetamide, and
N-(5-hydroxy-6-chloro-1-naphthyl)-2-aminoacetamide.

Representative electron transfer agents of structure (III) include:
N-(6-hydroxy-2-naphthyl)acetamide,
N-(6-hydroxy-5-fluoro-2-naphthyl)acetamide,
N-(6-hydroxy-7-fluoro-2-naphthyl)acetamide,
N-(6-hydroxy-5,7-difluoro-2-naphthyl)acetamide,
N-(6-hydroxy-5-chloro-2-naphthyl)acetamide,
N-(6-hydroxy-5,7-dichloro-2-naphthyl)acetamide,
N-(6-hydroxy-7-bromo-2-naphthyl)acetamide,
N-(6-hydroxy-5,7-dibromo-2-naphthyl)acetamide,
N-(6-hydroxy-5-cyano-2-naphthyl)acetamide,
N-(6-hydroxy-5,7-dicyano-2-naphthyl)acetamide,
N-methyl-N-(6-hydroxy-5-chloro-2-naphthyl)acetamide,
N-methyl -N-(6-hydroxy-7-chloro-2-naphthyl)acetamide,
N-methyl-N-(6-hydroxy-5,7-dichloro-2-naphthyl)acetamide,
N-(6-methoxy-2-naphthyl)acetamide,
N-(6-methoxy-5-chloro-2-naphthyl)acetamide,
N-(6-methoxy-5,7-dichloro-2-naphthyl)acetamide,
N-(6-hydroxy-2-naphthyl)-2-chloroacetamide,
N-(6-hydroxy-7-chloro-2-naphthyl)-2-chloroacetamide,
N-(6-hydroxy-2-naphthy 1 )-2,2-dichloroacetamide,
N-(6-hydroxy-7-chloro-2-naphthyl)-2,2,2-trichloroacetamide,
N-(6-hydroxy-2-naphthyl)-2-hydroxyacetamide,
N-(6-hydroxy-5-chloro-2-naphthyl)-2-methoxyacetamide,
N-(6-hydroxy-2-naphthyl)-2-aminoacetamide, and
N-(6-hydroxy-5,7-dichloro-2-naphthyl)-1-aminoacetamide.

Representative compounds of structure (IV) include:
N-(4-hydroxy-1-naphthyl)acetamide,
N-(4-hydroxy-5-chloro-1-naphthyl)acetamide,
N-methyl-N-(4-hydroxy-3-chloro-1-naphthyl)acetamide,
N-(4-methoxy-1-naphthyl)acetamide,
N-(4-hydroxy-1-naphthyl)-2-chloroacetamide,
N-(4-hydroxy-3-chloro-1-naphthyl)-2-chloroacetamide,
N-(4-hydroxy-1-naphthyl)-2,2-dichloroacetamide,
N-(4-hydroxy-5-chloro-1-naphthyl)-2-methoxyacetamide,
N-(4-hydroxy-5-chloro-1-naphthyl)-2-aminoacetamide,
N-(4-hydroxy-3-chloro-1-naphthyl)-2-aminoacetamide, and
N-(4-hydroxy-3-fluoro-1-naphthyl)acetamide.

The most preferred electron transfer agent is 3'-chloro-4'-hydroxyacetanilide.

These electron transfer agents can be prepared generally from known starting materials as follows:

In general, the halogenated compounds of Structures (I)–(IV) are prepared by halogenation of the known precursor anilide (for example, 4'-hydroxy- or alkoxyacetanilide, or an anilide of naphthalene) with a known halogenating agent such as sulfuryl chloride, sulfuryl bromide, or the free halogen in the presence of acid. Where the desired precursor is not available, an appropriately substituted phenol or naphthol can be nitrated by mild nitration using known techniques (for example, with nitric acid in a solvent such as glacial acetic acid) followed by hydrogenation, typically over platinum or paladium to produce the amine (see *J. Am. Chem. Soc.* 49, 1093, 1927). The amine is then acylated, for example, by condensation with the desired acylating agent such as an anhydride (for example, acetic anhydride) or an acid chloride such as acrylic acid chloride, to produce the anilide. Suitable acylation procedures are also described by Challis et al, *The Chemistry of Amides*, pp. 731–857, Interscience Publishing, New York, 1970. If the selected starting materials do not already provide the requisite electron withdrawing groups, the resulting anilide can be conveniently halogenated as described above. Alternatively, the amine precursor to the anilide can be acylated with an acylating agent that provides the group at $R^2$ (for example, trichloroacetic acid chloride or maleic anhydride), or the aromatic ring of the anilide can be alkylated, acylated or nitrated at the $R^4$ or $R^5$ (or both) positions using known techniques to provide the requisite electron withdrawing groups from $R^4$ and $R^5$.

An optional but preferred component of the signal-providing composition of this invention is a low molecular weight cationic surfactant to provide micelles, or a cationic polymer to provide a hydrophobic environment for increased sensitivity, storage stability and kinetic stability.

Surfactants are generally compounds which lower the surface tension of water, as is well understood by one skilled in the art. Generally, such materials are synthetic, but some are naturally occurring. Cationic surfactants have a net positive charge and are described in a number of publications including, for example, *Surfactants and Interfacial Phenomena*, By Milton J. Rosen, John Wiley and Sons, N.Y., 1978, pages 13–17 and are identified by tradenames in *McCutcheon's Emulsifiers and Detergents*, North American Ed., MuCutcheon's Division, The Manufacturing Confectioner Publishing Co., 1988, page 259. Positive charges in the surfactants can be provided by cationic groups including, but not limited to, quaternary ammonium, quaternary phosphonium, sulfonium, pyridinium, pyrimidinium, imidazolium and oxonium.

Particularly useful cationic surfactants and polymers can be represented by the structure (VIII):

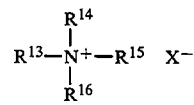

wherein $R^{13}$ is substituted or unsubstituted alkyl of at least 7 carbon atoms, and preferably from 10 to 20 carbon atoms (such as n-octyl, isononyl, isodecyl, dodecyl, tetradecyl, hexadecyl, octadecyl, eicosyl, 2,7,8-trimethyldecyl, 4-ethyl-6-methyldodecyl, benzyl and phenethyl), substituted or unsubstituted aryl of 6 to 14 carbon atoms in the aromatic nucleus (such as phenyl, naphthyl or anthryl) which can be substituted with one or more hydrophobic groups such as linear or branched alkyl of 1 to 10 carbon atoms (such as methyl, ethyl, isopropyl, e,uns/t/ -butyl, hexyl, octyl, isooctyl, nonyl or isononyl), halo and others known to one skilled in the art. Such substituted aryl groups include, but are not limited to xylyl, tolyl, isononylphenyl, dimethylphenyl and trichlorophenyl. $R^{13}$ can also be substituted or unsubstituted alkenyl of 8 to 20 carbon atoms (such as 1-octenyl, 1-decenyl and 2-dodecenyl), or a polymeric moiety (described below).

Preferably, $R^{13}$ is alkyl or alkenyl of 14 to 16 carbon atoms, with groups such as 2,4-dimethyl-6-ethyldecyl, tetradecyl and hexadecyl being more preferred.

In structure (VIII), $R^{14}$ can be alkyl or alkenyl as defined for $R^{13}$, substituted or unsubstituted alkyl of 1 to 7 carbon atoms (such as methyl, ethyl, isopropyl, e,uns/t/ -butyl, methoxymethyl, benzyl and hexyl), substituted or unsubstituted alkenyl of 2 to 7 carbon atoms (such as a ethenyl, allyl, isopropenyl and n-butenyl), or carbocyclic aryl of 6 to 10 carbon atoms in the ring system (such as phenyl, tolyl, xylyl, naphthyl and p-methoxyphenyl). One of $R^{14}$, $R^{15}$ and $R^{16}$ can be one of the nonpolymeric groups defined above for $R^{10}$.

$R^{15}$ and $R^{16}$ are independently substituted or unsubstituted alkyl of 1 to 7 carbon atoms (such as methyl, ethyl, isopropyl, e,uns/t/ -butyl, methoxymethyl, benzyl and hexyl), substituted or unsubstituted alkenyl of 2 to 7 carbon atoms (such as a ethenyl, isopropenyl and allyl), or carbocyclic aryl of 6 to 10 carbon atoms in the ring system (such as phenyl, tolyl, xylyl, naphthyl and p-methoxyphenyl).

Alternatively, any two or three of $R^{14}$, $R^{15}$ and $R^{16}$ can be taken together to represent sufficient carbon atoms and an oxygen, nitrogen or sulfur atom to complete, with the quaternary ammonium atom, a 5- to 6-membered heterocyclyl cationic group. Examples of such groups include, but are not limited to pyridinium, piperidinium, pyrrolidinium, morpholinium, quinolinium, pyrimidinium, acridinium, benzothiazolium, benzoxazolinium and imidazolium.

Preferably, $R^{14}$, $R^{15}$ and $R^{16}$ are independently methyl or ethyl.

$Y^-$ is a suitable monovalent acid anion which is not a substrate or inhibitor for peroxidases, including but not limited to, perchlorate, halide (such as fluoride, chloride and bromide), tetrafluoroborate, triflate, methyl sulfate, hexafluorophosphate, nitrate, ptoluenesulfonate and others readily apparent to one skilled in the art. Halide anions are preferred.

Examples of useful nonpolymeric cationic surfactants are hexadecyltrimethylammonium chloride, dodecyltrimethylammonium chloride, cetyltrimethylammonium bromide (also known as hexadecyltrimethylammonium bromide), cocotrimethylammonium chloride, tallowtrimethylammonium chloride, soyatrimethylammonium chloride, myristyltrimethylammoniumbromide, stearyltrimethylammonium chloride, cetylethyldimethylammoniumbromide, didodecyldimethylammoniumbromide, cetylpyridinium chloride and myristyldimethylbenzylammonium chloride.

Cetyltrimethylammonium bromide is most preferred.

Many of these surfactants are readily available from a number of commercial sources. Others can be readily prepared by a skilled chemist using known starting materials and procedures.

Where $R^{13}$ in structure (VIII) is a polymeric moiety, the backbone of such polymers can be conventional polyesters, polyamides, polyethyleneimines, polycarbonates, cellulosic materials, and vinyl addition homo- and copolymers comprised of recurring units of a monomer having the desired positive charge. These materials can be prepared from conventional materials using conventional procedures. The polymer can have the charges incorporated therein from starting materials, or from chemical reaction after preparation.

Particularly useful cationic polymers are vinyl addition homo- or copolymers prepared from ethylenically unsaturated polymerizable monomers having the requisite positively charged groups, and one or more comonomers which provide hydrophobic regions characteristic of surfactants, crosslinked regions or other suitable properties.

Representative cationic monomers include, but are not limited to, N-cyclohexyl-N,N-dimethyl-N-(m- & p-vinylbenzyl)ammonium chloride, N-benzyl-N,N-dimethyl-N-(m- & p-vinylbenzyl)ammonium chloride, 3-(2-hydroxypropyl)-1-vinylimidazolium chloride and 1-methyl-4-vinylpyridinium chloride. Useful comonomers include, but are not limited to, styrene and its derivatives (such as vinyltoluene and p-t-butylstyrene), acrylic and methacrylic acid esters (such as methyl acrylate, methyl methacrylate, butyl acrylate and butyl methacrylate), crosslinkable monomers {such as divinylbenzene, ethylene diacrylate, ethylene dimethacrylate and N,N'-methylenebis(acrylamide)]. Other useful polymers are described, for example, as mordants in U.S. Pat. No. 4,069,017 (Wu et al) and U.S. Pat. No. 4,024,839 (Wu et al). Such materials generally have quaternary ammonium or quaternary phosphonium groups pendant from the polymer backbone, and preferably at least from about 40 to 100 weight percent of the ethylenically unsaturated polymerizable monomer derived recurring units have such groups. The remaining recurring units can be derived from a wide variety of ethylenically unsaturated polymerizable monomers as noted in the patents identified above.

Representative cationic polymers include, but are not limited to, poly(N,N,N-trimethyl-N-vinylbenzylammonium chloride), poly[styrene-co-benzyl-N,N-dimethyl-N-(m- & p-vinylbenzyl)ammonium chloride-co-divinylbenzene], poly(N,N,N-trioctyl-N-vinylbenzylphosphonium chloride), poly[styrene-co-N-vinylbenzyl-N,N,N-trihexylammonium chloride], poly (styrene-co-N,N,N-trimethyl-N-vinylbenzylammonium chloride), poly[N-cyclohexyl-N,N-dimethyl-N-(m- & p-vinylbenzyl)ammonium chloride], poly[styrene-co-1vinylimidaidazole- co-3-(2-hydroxyethyl)-1-vinylimidazolium chloride] and others readily apparent to one skilled in the art. A preferred cationic polymer is poly[N-cyclohexyl-N,N-dimethyl-N-(m- & p-vinylbenzyl)ammonium chloride].

The signal-providing composition of this invention is generally buffered to a pH of from about 5 to about 10 using one or more suitable buffers well known in the art. For example, buffers such as tris(hydroxymethyl)aminomethane, borate, phosphate, bis-tris-propane and tricine can be used. Tris(hydroxymethyl)aminomethane and phosphate are preferred. Where the signal generating reagent is a DPD and the signal to be produced is light, the pH is generally from about 7 to about 9.5, whereas where a colorimetric signal is to be generated using a leuco dye, tetrazolium salt or diazonium salt, the pH is generally from about 5 to about 9.

In the signal-providing composition of this invention, the amounts of each component can be varied depending upon where it is intended for use, the particular sensitivity of the reagents and other factors well understood by one skilled in the art. Thus, the following general ranges are meant to provide guidance for the skilled worker, and not to limit the practice of this invention.

The amount of buffer would be readily apparent to a skilled worker since it is well known how much of any buffer is needed to maintain a desired pH. The amount of signal generating reagent is generally at least about 0.01 mmolar, with an amount in the range of from about 0.1 to about 10 mmolar being preferred. The electron transfer agent having structure (I), (II), (III) or (IV) is generally present in an amount of at least about 0.01 mmolar, with an amount in the range of from about 0.05 to about 10 mmolar being preferred.

When used, the nonpolymeric cationic surfactant is present in an amount which is from about 0.05 to about 0.25% above its critical micelle concentration. This can be readily determined for a given surfactant since the "critical micelle concentration" for many surfactants is well known, or can be readily determined using procedures described, for example, in *Surfactant Science and Technology*, Meyers, VCH Publishers, New York, Chapter 3, 1988. If a cationic polymer is included in the composition, it is present in an amount of from about 0.01 to about 2% (by weight).

This invention also provides a peroxidase-containing aqueous composition which contains a peroxidase in free form, or as a label conjugated with a specific binding molecule (such as an antibody, avidin or biotin), and the electron transfer agent described herein. Such a composition can also be buffered as described for the signal-providing composition of this invention. The amounts of peroxidase or peroxidase-labeled specific binding molecule and electron transfer agent present in this composition would be readily apparent to one skilled in the art.

Besides the compositions described above, the present invention also provides a kit of individually packaged reagents, equipment and instructions useful for carrying out a variety of analytical methods (described below). The packaging of kit components is well known in the art.

In one embodiment, a kit comprises, individually packaged: the signal-providing composition described above, and a peroxidase or peroxidase-labeled specific binding molecule. By "specific binding molecule" is meant any biological or chemical compound which will specifically bind with a receptor therefor which will not bind with other materials. Particularly useful labeled specific binding species are peroxidase-labeled proteins or oligonucleotides. Such proteins include antibodies and avidin. Suitable receptors for given specific binding species are well known. Other components useful in an assay (such as an oxidant, described below) can be included in the test kit.

Another kit can include the peroxidase-containing compositions as defined above, and a separately packaged signal generating reagent.

As used herein, "peroxidase" is meant to be any peroxidative substance (enzymatic or otherwise) which catalyzes the oxidation of a substrate, such as luminol or a leuco dye, to produce the appropriate signal. Microbial, fungal and plant peroxidases are preferred with horseradish peroxidase being most preferred. The amount of peroxidase can vary widely due to the amount of other components used in the reaction. A useful amount would be readily apparent to one skilled in the art, but a minimum amount would generally be at least about $1 \times 10^{-7}$ I.U./ml (or equivalent amount for nonenzymatic peroxidative substances). I.U. represents the International Unit for enzyme activity and is defined as the amount of enzyme activity required to catalyze the conversion of 1 micromole of substrate to product per minute under standard pH and temperature conditions.

An oxidant is needed to produce the desired signal in the presence of peroxidase and the electron transfer agent of structure (I), (II), (III) or (IV). Various useful oxidants are known, but perborate ion and hydrogen peroxide are preferred with the latter being most preferred. The amount of oxidant used in a given assay is readily apparent to one skilled in the art, but a minimum amount of about 0.1 mmolar is generally used.

Another embodiment of a test kit can include, in individual packaging, a signal generating reagent as described herein, and an electron transfer agent having structure (I), (II), (III) or (IV), and any additional optional components as would be readily understood by one skilled in the art. In some methods of this invention, peroxidase is used in "free form" (non-conjugated) for clinical analysis. In specific binding methods, however, the peroxidase is used as a conjugate with a specific binding ligand or receptor therefor, or with a specific binding molecule which is reactive with either the ligand or receptor. The ligand and receptor are complexed in such assays and thereby labeled with the peroxidase for eventual detection of the complex or uncomplexed materials. The preparation of such conjugates can be achived using a variety of known techniques (for example, as described by Yoshitake et al, *Eur. J. Biochem.*, 101, 395, 1979, and in U.S. Pat. No. 5,106,732 of Kondo et al).

Various specific binding assay formats are useful in the practice of this invention, and include nucleic acid hybridization assays, immunochemical assays (such as enzyme immunoassays, sandwich assays, competitive binding assays, direct binding assays) and others well known in the art. Such assays are generally described, for example in U.S. Pat. No. 4,598,044, U.S. Pat. No. 4,745,077 (Holian et al), U.S. Pat. No. 5,077,198 (Shih et al), U.S. Pat. No. 5,085,986 (Mauck et al), Matthews et al, *Anal.Biochem*, 169, pages 1–25 (1988), and WO 88/01302 (published Feb. 25, 1988). The method of the invention can be preceeded by an amplification process, such as polymerase chain reaction (commonly known as PCR) as described for example in U.S. Pat. No. 4,965,188 (Mullis et al) and ligase chain reaction which is generally described by Weiss, *Science*, 251, pages 1292-3, 1991 to increase the amount of targeted nucleic acid which can then be detected using the composition of this invention.

Thus, the method of this invention can be used to detect any of a wide variety of chemical and biological materials, such as amino acids, peptides, polypeptides, proteins (including enzymes, avidin, antibodies and antigenic proteins), carbohydrates (including monosaccharides, polysaccharides and lipopolysaccharides), hormones (such as human chorionic gonadotropin, thyroid stimulating hormone, leutinizing hormone, thyroxin, follicle stimulating hormone, parathyroid hormone and growth hormone), metabolites (such as glucose, lactate and pyruvate), oligonucleotides, nucleic acids, vitamins (such as $B_{12}$ and biotin), intact cells from various organisms (including microorganisms) and drugs (narcotics, therapeutic and those abused).

Particularly useful specific binding methods of this invention are those known in the art as sandwich assays whereby the ligand of interest is complexed with at least a first and second receptor either simultaneously or in a desired sequence. One of the receptors is insolubilized on a suitable support (such as microtiter plate, polymeric, magnetic or glass particles, film, membrane, filter paper and others known in the art) by adsorption, covalent or other known attachment procedures, or is capable of being insolubilized through further complexation or reaction. For example, the receptor can be labeled with a specific binding moiety (for example, biotin) which is reactive with its corresponding receptor moiety (for example, avidin) which is insolubilized on the support.

In the sandwich assays, the second receptor for the ligand of interest can be labeled with peroxidase, or is capable of being so labeled through additional specific binding reactions (such as labeling the ligand through an avidin-biotin complex). Detection of the label is accomplished using the composition described above.

In more preferred embodiments, the ligand of interest is an antigenic material with which antibodies are reactive, or a nucleic acid with which complementary nucleic acids (such as oligonucleotides) can be hybridized.

The assays described above can be carried out in solution or in a dry format. Solution assays generally refer to methods carried out in solution in a suitable container, and in the case of heterogeneous specific binding assays, suitable separation techniques and equipment are then used to separate unbound materials from the bound materials. In dry assays, chemical or specific binding reactions can be carried out in a dry element, test strip or fibrous sheet and the presence of the analyte is detected by adding the stabilized chemiluminescent composition of this invention. For example, a specific binding reaction can be carried out using a peroxidase-labeled specific binding material which is used to generate a chemiluminescent signal. Details regarding such elements are well known in the art, including for example, U.S. Pat. No. 3,992,158 (Przybylowicz et al), U.S. Pat. No. 4,258,001 (Pierce et al), U.S. Pat. No. 4,292,272 (Kitajima et al), U.S. Pat. No. 4,430,436 (Koyama et al) and U.S. Pat. No. 4,670,381 (Frickey et al).

The following examples are provided to illustrate the practice of this invention, but are not intended to be limiting. All percentages are by weight, unless otherwise noted.

Except where noted, all reagents and equipment were obtained from Eastman Kodak Company or other commercial sources.

The following preparations describe representative procedures for making the electron transfer compounds useful in the practice of this invention.

Preparation A

Into a 1 liter round bottom flask (fitted with a magnetic stirrer), glacial acetic acid (700 ml) was mixed with 4'-hydroxyacetanilide (50 g) until the solid was completely dissolved. The resulting solution was cooled to between 10°–15° C., and to it was added $SO_2Cl_2$ (47 g) and the resulting solution was stirred for 1 hour. Water (200 ml) was then added, and 3'-chloro-4'-hydroxyacetanilide crystallized as a white precipitate (60 g, 98% yield).

Preparation B

Into a 500 ml round bottom flask (fitted with a magnetic stirrer), water (200 ml) was mixed with 4-amino-2,6-dichlorophenol hydrochloride (20 g) until the solid was completely dissolved. The resulting solution was warmed to 70° C., and to it was added acetic anhydride (11 g) and the resulting solution was stirred for 1 hour. Upon cooling, crystals of 3', 5'-dichloro-4'-hydroxyacetanilide formed (19.6 g, 95% yield).

Preparation C

Into a 500 ml round bottom flask (fitted with a magnetic stirrer), a 50:50 mixture of water:ethanol was combined with 5-amino-1-naphthol (20 g, 125 mmole) until the solid was completely dissolved. The solution was warmed to boiling and to it was added acetic anhydride (14 g) and the resulting solution was stirred for 1 hour. Upon cooling, crystals of N-(5-hydroxyl-napthyl)acetamide (21 g, 84% yield) formed.

Preparation D

Into a high pressure reaction vessel (fitted for shaking), tetrahydrofuran (200 ml) was combined with 6-bromo-2-naphthol. The reaction vessel was then charged with gaseous ammonia (800 psi, 56.2 kg/cm$^2$) and warmed to 80° C. for 3 days. The resulting solution was removed by reduced pressure and some of the solid precipitate 6-amino-2-napthol (10 g) was placed (without further purification) into a 500 ml round bottom flask). The solid was completely dissolved into a 50:50 mixture of water:ethanol. The resulting solution was warmed to boiling and acetic anhydride (7 g) was added. After 1 hour of continuous stirring, the solution was cooled and crystals of N-(6-hydroxy-2-naphthyl)acetamide formed (8 g, 63% yield).

Preparation E

Into a 500 ml round bottom flask (fitted with a magnetic stirrer), a 50:50 mixture of water:ethanol was combined with 4-amino1-naphthol (20 g, 125 mmole) until the solid was completely dissolved. The solution was warmed to boiling, and to it was added acetic anhydride (14 g) and the resulting solution was stirred for 1 hour. Upon cooling, crystals of N-(4-hydroxy-1-naphthyl)acetamide (20 g, 79% yield) formed.

EXAMPLES 1–2

Aqueous Chemiluminescent Compositions

An aqueous composition for providing a chemiluminescent signal was prepared as follows:

A buffer solution was prepared, containing diethylenetriaminepentaacetic acid (100 μmolar) in tris(hydroxymethyl)aminomethane buffer (0.1 molar, pH Solution 1 was prepared by mixing luminol, sodium salt (8 mg/10 ml, 4 mmolar) and 3'-chloro-4'-hydroxyacetanilide (0.75 mg/10 ml, 0.4 mmolar) in the buffer solution. Solution 2 contained 9.07 μl of a 30% stock solution of hydrogen peroxide in the buffer solution (10 ml).

A composition of this invention was prepared by adding horseradish peroxidase (1 μl of 2 pmolar solution) to the buffer solution (199 μl) and Solution 1 (100 μl). To this mixture was added Solution 2 (100 μl) to provide a chemiluminescent composition of this invention. The final concentrations were as follows: luminol (1 mmolar), hydrogen peroxide (2 mmolar), 3'-chloro-4'-hydroxyacetanilide (100 μmolar) and horseradish peroxidase (5 femtomolar).

A second composition of this invention (Example 2) was like Example 1 except hexadecyltrimethylammonium bromide (0.1%) was also added.

EXAMPLE 3

Aqueous Colorimetric Composition

An aqueous composition of this invention was prepared containing 2-(4-hydroxy-3-methoxyphenyl)-4,5-bis(4-methoxyphenyl)imidazole leuco dye (0.008%), poly(vinyl pyrrolidone) (1%), sodium phosphate (10 mmolar, pH 6.8), diethylenetriaminepentaacetic acid (10 μmolar), hydrogen peroxide (10 mmolar) and 3'-chloro-4'-hydroxyacetanilide (5 mmolar).

EXAMPLE 4

Assay for Horseradish Peroxidase

The composition of Example 1 (400 μl) was placed in a commercially available Turner TD 20e Luminometer to evaluate the chemiluminescent signal in response to the presence of horseradish peroxidase. The data was collected as 10 second intervals of the Turner light signal, expressed as relative light units.

A Control composition was similarly prepared and tested, except the 3'-chloro-4'-hydroxyacetanilide was replaced with 4'-hydroxyacetanilide.

The resulting chemiluminescence signals from both compositions are plotted on the "Y" axis in FIG. 1, as measured at 25° C. over a period of twenty minutes ("X" axis). The plot for the Control is labeled as "1" and the plot for the invention is labeled as "2". It is clear that higher signal is provided by the use of the composition of this invention.

Figure 2:
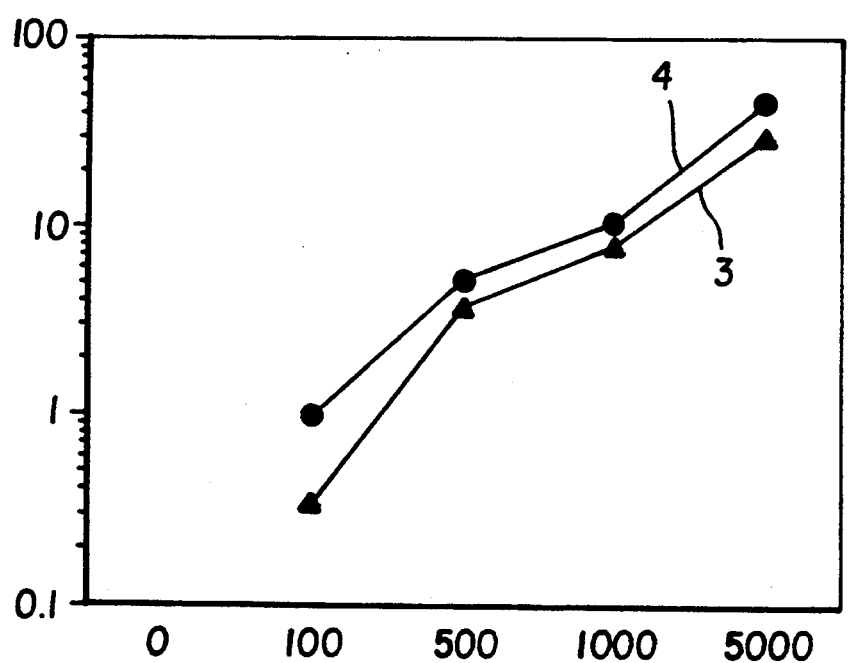
FIG. 2 is a graphical representation of chemiluminescent signal obtained using a composition of this invention and a Control composition at various concentrations of horseradish peroxidase, as described in Example 4 below.

Similar chemiluminescent signals were generated at various concentrations (100 to 5000 attomoles) of horseradish peroxidase. The results are shown in FIG. 2 where the Control plot is labeled as "3" while the invention plot is labeled as "4". The results, as shown in FIG. 2 (signal vs. enzyme concentration), make it evident that 3'-chloro-4'-hydroxyacetanilide provided an improvement at each concentration.

EXAMPLE 5-7

Use of Several Electron Transfer Agents to Detect Hydrogen Peroxide

A solution (300-"x" μl) of hydrogen peroxide (2 mmolar), luminol (1 mmolar) and each electron transfer agent and diethylenetriaminepentaacetic acid (100 μmolar) in tris(hydroxymethyl)aminomethane hydrochloride (0.05 molar, pH 8) was prepared and added to individual test wells of a microtiter plate. Example 5 contained 3'-bromo-4'-hydroxyacetanilide (0.15 mmolar), Example 6 contained 3'-chloro-4'-hydroxyacetanilide (0.15 mmolar), and Example 7 contained 3',5'-dichloro-4'-hydroxyacetanilide (2 mmolar).

At the beginning of the assay (time "zero"), aliquots ("x" μl) of commercially available Sigma XII horseradish peroxidase (0 to 100,000 attomoles) in buffer were added to each test well of the microtiter plate so that each final cup volume was 300 μl. After five minutes, the chemiluminescent signal was determined using a TITERTEK LUMINOSKAN TM reader using a 10 second integration time.

A Control assay was similarly carried out using 4'-hydroxyacetanilide as the electron transfer agent (0.15 mmolar).

Figure 3:
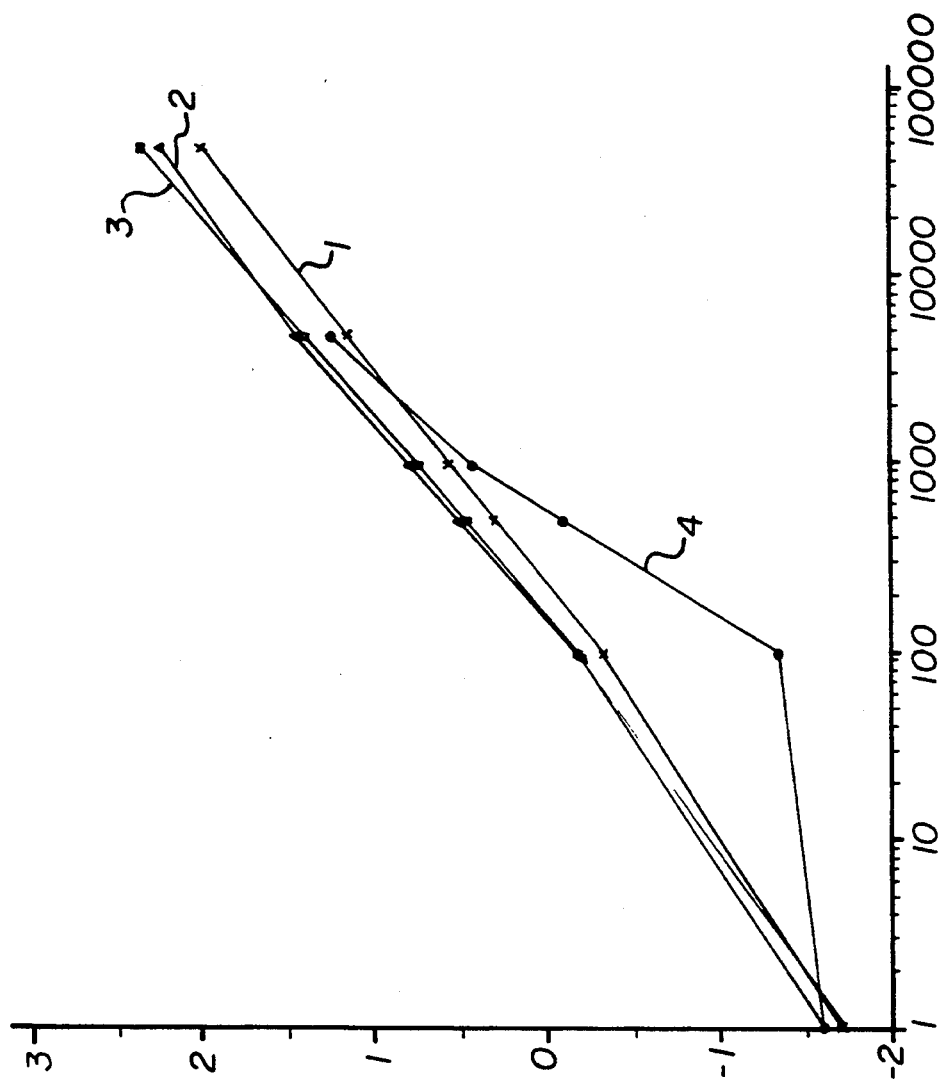
FIG. 3 is a graphical representative of chemiluminescent signal obtained in assays versus the concentration of enzyme label, as described in Examples 5–7 below.

The results are illustrated in FIG. 3 which is a plot of log (chemiluminescence signal-5 minutes) versus log (horseradish peroxidase concentration, attomoles). The plot identified as "1" was for the Control assay, the plot identified as "2" was for Example 5, the plot identified as "3" was for Example 6, and the plot identified as "4" was for Example 7.

Examples 5 and 6 provided a higher chemiluminescent signal over the five minute assay period as opposed to the Control assay. Example 7 showed a lower chemiluminescent signal than the Control assay, but it demonstrated less variation in chemiluminescence over time than the Control assay.

Example 8

Solution Immunoassay for Thyroid Stimulating Hormone (TSH)

This example demonstrates the practice of this invention for the detection of TSH in a biological specimen. The assay was carried out using a commercially available AMERLITE TM Fast TSH immunoassay kit, plate washer/incubator and chemiluminescence reader. The chemiluminescent signal was generated using a commercial AMERLITE TM solution of 4-iodophenol, sodium perborate and luminol in borate buffer (pH 8.5) for the Control assay, or using a solution of 3'-chloro-4'-hydroxyacetanilide (0.15 mmolar), luminol (1 mmolar), hydrogen peroxide (2 mmolar), diethylenetriaminepentaacetic acid (0.1 mmolar) and cetyltrimethylammonium bromide (0.1%) in tris(hydroxymethyl)aminomethane hydrochloride buffer (0.05 molar, pH 8) for the assay of this invention.

The protocol described in the commercial AMERLITE TM Fast TSH kit noted above was followed:
1) A specimen containing 0-200 μI.U./ml of TSH was added to a test well of the kit test device containing anti-TSH monoclonal antibodies adsorbed to the walls thereof.
2) Anti-β-TSH-horseradish peroxidase conjugate of the commercial kit was added to the nest well to form a ternary complex.
3) Incubation was carried out at 37° C. for about 30 minutes.
4) Unbound materials were washed from the test well using the commercial kit wash solution.
5) The solution (described above) for generating the chemiluminescent signal was then added, and the resulting signal was evaluated after 5 minutes.

Figure 4:
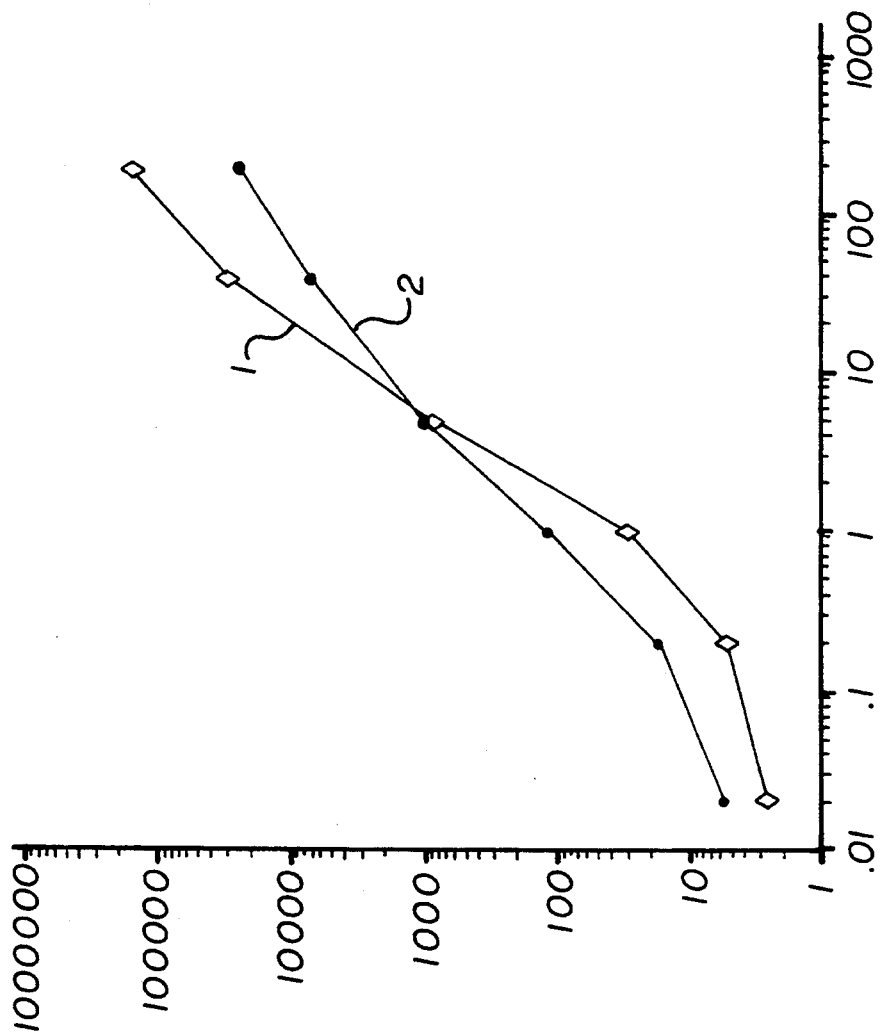
FIG. 4 is a graphical representation of chemiluminescent signal obtained in assay for thyroid stimulating hormone (TSH), as described in Example 8 below.

The resulting signals for both the Control and invention were acceptable for calibration, but the invention assay provided improved sensitivity at the lower TSH levels (that is, from 0-5 μI.U./ml). This distinction is important for clinical differentiation between a hyperthyroid and euthyroid status of a patient. These results are illustrated in FIG. 4 which contains graphical plots of log(light units) versus log(TSH concentration, μI.U./ml). The plot identified as "1" is the Control assay, and the plot identified as "2" is the assay of this invention.

EXAMPLE 9

Immunoassay for *Chlamydia trachomatis*

This example shows the practice of the present invention for the determination of *C. trachomatis* in a biological specimen and compares it to a Control assay for the same analyte using 4'-hydroxyacetanilide as the electron transfer agent.

The following materials and compositions were used in the assays of this example.

The microporous membrane used in the assays was an uncharged and uncoated nylon 66 membrane commercially available as LOPRODYNE TM membrane from Pall Corporation. The membrane was mounted in each of the three test wells of a commercially available SURECELL ™ test device (Eastman Kodak Company). Specimens for testing were obtained from female patients using endocervical swabs. Each specimen was tested using a separate test device.

A conventional flexible extraction tube was used to extract antigen from *C. trachomatis* organisms in the specimens, the tube having at separate locations on the inside thereof, dried coatings: (1) tris(hydroxymethyl)aminomethane buffer (20 μl of a 1.65 molar solution, pH 11) with thimerosal preservative (0.01%), and (2) 2-(N-morpholino)ethane sulfonic acid (10 mmolar, 50 μl solution, pH 6), sodium azide (1.54 molar), ethylenediaminetetraacetic acid (5.4 mmolar), 5,5-dimethyl-1,3-cyclohexanedione (21.4 mmolar), dithiothreitol (0.188 molar) and poly(acrylamide) (6.35%).

Composition 1 contained AMIDECK ™ protease (4 mg/ml, 170 units/mg, Genencor, International) in 2-(N-morpholino)ethane sulfonic acid buffer (10 mmolar, pH 6), sodium chloride (50 mmolar), calcium chloride (5 mmolar), 1,2-propanediol (10% w/v) and thimerosal (0.01%).

An antigen extraction composition contained ethanolamine hydrochloride (0.47 molar), sodium chloride (0.27 molar), thimerosal (30 mmolar), ethylenediaminetetraacetic acid (50 mmolar), EMCOL ™ CC-36 cationic surfactant (0.45%, Witco Chemical) and sodium hydroxide (0.66 normal, to provide pH 13.5).

Composition 2 contained hydrogen peroxide (12% in water), diethylenetriaminepentaacetic acid (10 μmolar) and thimerosal (0.01%).

A wash solution contained 3-cyclohexylamino-2-hydroxy-1-propanesulfonic acid buffer (0.05 molar, ph 10), EMCOL ™ CC-9 cationic surfactant (0.75%) and thimerosal (0.01%).

Composition 3 contained creatine kinase-MB F(ab')$_2$ antibody fragment conjugated to horseradish peroxidase (5 μg/ml), casein (0.01%), LONZAINE ™ C amphoteric surfactant (0.01%, Lonza Corp.) and thimerosal (0.01%) in phosphate buffered saline solution (pH 7.2). This composition was used in a test well of each test device as a negative control. The labeled antibody fragment was prepared using known procedures (EPA-0 456 309) including a final chromatography step using a standard DEAE column and (1) tris(hydroxymethyl)aminomethane (20 mmolar, pH 8), and (2) tris(hydroxymethyl)aminomethane (20 mmolar, pH containing sodium chloride (0.75 molar) as eluting buffers.

A horseradish peroxidase labeled F(ab')$_2$ anti-chlamydial labeled antibody fragment was prepared using known procedures (EPA-0 456 309) (4 μg/ml of solution, final concentration) was mixed in solution with casein (0.05%), LONZAINE ™ amphoteric surfactant (0.01%, Lonza Corp.), and thimerosal (0.01%) in phosphate buffered saline solution (pH 7.2).

The dye-providing composition used for the assay of this invention was that of Example 3. In the Control assay, a similar dye-providing composition was prepared and used, that composition containing 4'-hydroxyacetanilide as the electron transfer agent.

Assay Protocol

In assaying each patient specimen, Composition 1 (7 drops) was added to the extraction tube and a swab containing each patient specimen was placed into the tube, rotated 10 seconds, followed by incubation of the tube for 1 minute at room temperature. The antigen extraction composition was then added to the tube, and the swab was rotated again for 10 seconds, and incubation was again carried out for 1 minute at room temperature. Composition 2 was then added, and the swab was rotated again for 10 seconds, followed by a third incubation for two minutes at room temperature. The swab was wrung out by squeezing the tube, and removed therefrom. The extraction procedure required about 4 to 5 minutes.

The resulting solution containing extracted lipopolysaccharide antigen from *C. trachomatis* was removed from the tube using a pipette, prefiltered, and transferred to each test well of each test device (4 drops per test well). Fluid was allowed to drain through the microporous membranes in the test wells. Each test well was then washed with the wash solution (4 drops per test well).

Composition 3 (2 drops) was then added to one of the test wells of each test device (considered a negative control test well). The composition containing enzyme-labeled anti-chlamydial antibody fragment (2 drops) was added to each of the two remaining test wells of each test device. One of those two test wells (considered a positive control test well) contained dried *C. trachomatis* lipopolysaccharide antigen on the membrane.

After incubation for two minutes at room temperature, the wash step was repeated twice. Each dye-providing composition was added to individual test devices and after one, two or three minutes incubation at room temperature, the test sample well in each test device was evaluated for dye signal on the membrane.

Figure 5:
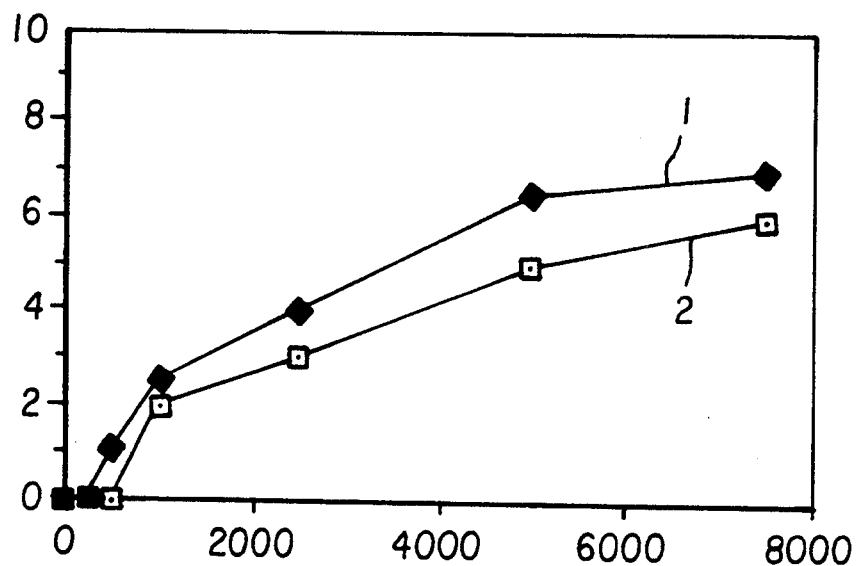
FIG. 5 is a graphical plot of dye signal versus *Chlamydia trachomatis* antigen concentration after 1 minute of incubation time as described in Example 9 below.
Figure 6:
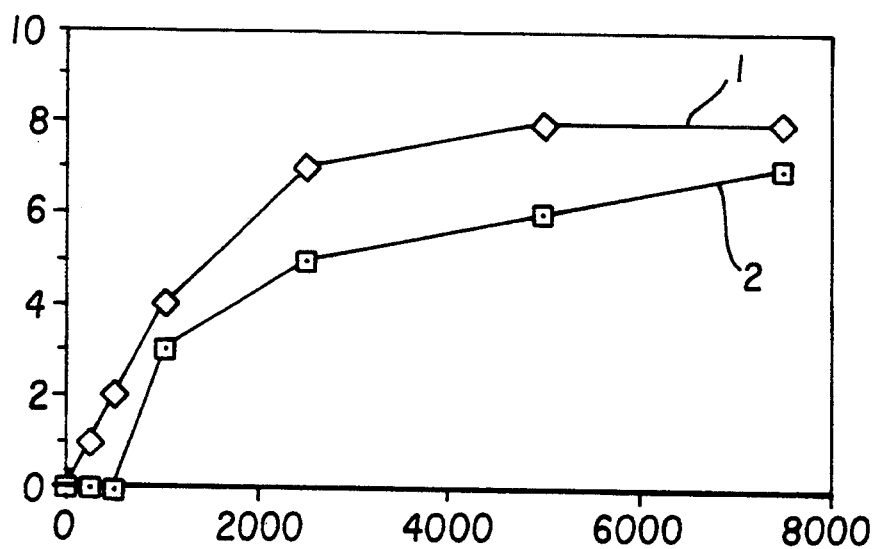
FIG. 6 is a graphical plot of dye signal versus *Chlamydia trachomatis* antigen concentration after 2 minutes of incubation time as described in Example 9 below.
Figure 7:
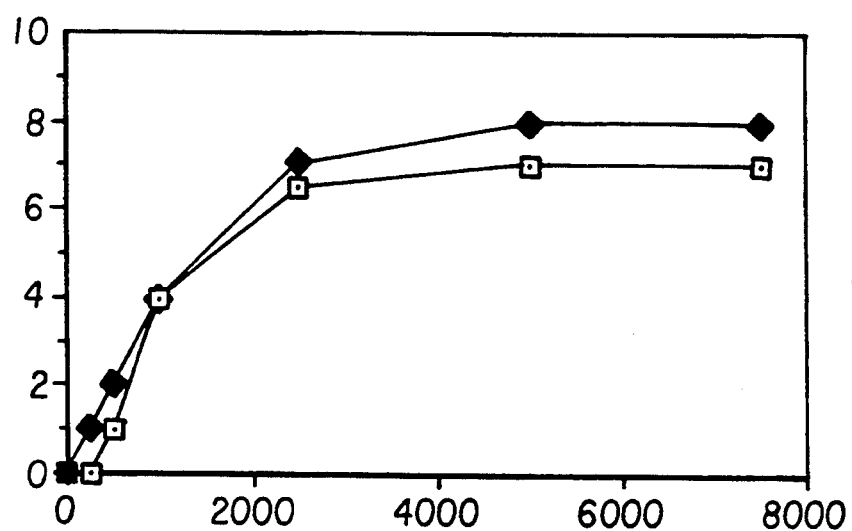
FIG. 7 is a graphical plot of dye signal versus *Chlamydia trachomatis* antigen concentration after 3 minutes of incubation time as described in Example 9 below.

The resulting dye signals are illustrated in FIGS. 5–7. In each FIGURE, dye signal is plotted versus antigen concentration (pg). The dye signal is determined from a color chart having values of dye density ranging from 0 (no density) to 10 (highest density). The results are shown for 1, 2 and 3 minute incubations in FIGS. 5, 6 and 7, respectively. In each FIGURE, the plot for the invention is labeled as "1" and the Control assay plot is labeled as "2".

It is apparent that the assay of the present invention using 3'-chloro-4'-hydroxyacetanilide as the electron transfer agent was more sensitive to the presence of various concentrations of antigen over the three different incubation time periods.

EXAMPLE 10

Comparative Example

The present example is a solution assay for peroxidase, and compares the present invention using 3'-chloro-4'-hydroxyacetanilide as an electron transfer agent with two Control assays (A and B) using 3'-methyl-4'-hydroxyacetanilide and 2'-methyl-4'-hydroxyacetanilide, respectively, as electron transfer agents.

The assay for peroxidase was carried out as a colorimetric rate assay in cuvettes (3 ml) using a Beckman DU-68 spectrophotometer. A stock dye solution containing 2-(4-hydroxy-3-methoxyphenyl)-4,5-bis(4-methoxyphenyl)imidazole leuco dye (0.008%) was prepared as described in Example 3, except no electron transfer agent was included. Specific amounts of electron transfer agent were then added to aliquots (25 ml) of the dye solution. Admixtures of the dye solution and the electron transfer agent solutions (10 mmolar) were then prepared to obtain 5 and 1 mmolar concentrations of the electron transfer agent in the resulting admixtures.

To start the assay, 3 ml of the test concentration of electron transfer agent (1, 5 or 10 mmolar) were added to a spectrophotometer cuvette. At time zero, horseradish peroxidase stock solution (10 μl, 3 nmolar in 50 mmolar phosphate buffer, pH 7 containing 0.01% ethylmercurithiosalicylic acid and 10 mmolar 4'-hydroxyacetanilide) was vortex-mixed into the cuvette solution (3 ml), and the resulting change in absorbance at 515 nm was measured. Initial rates of absorbance change from 0 to 50 seconds were calculated as dA/dT (milliabsorbance units/minute).

Figure 8:
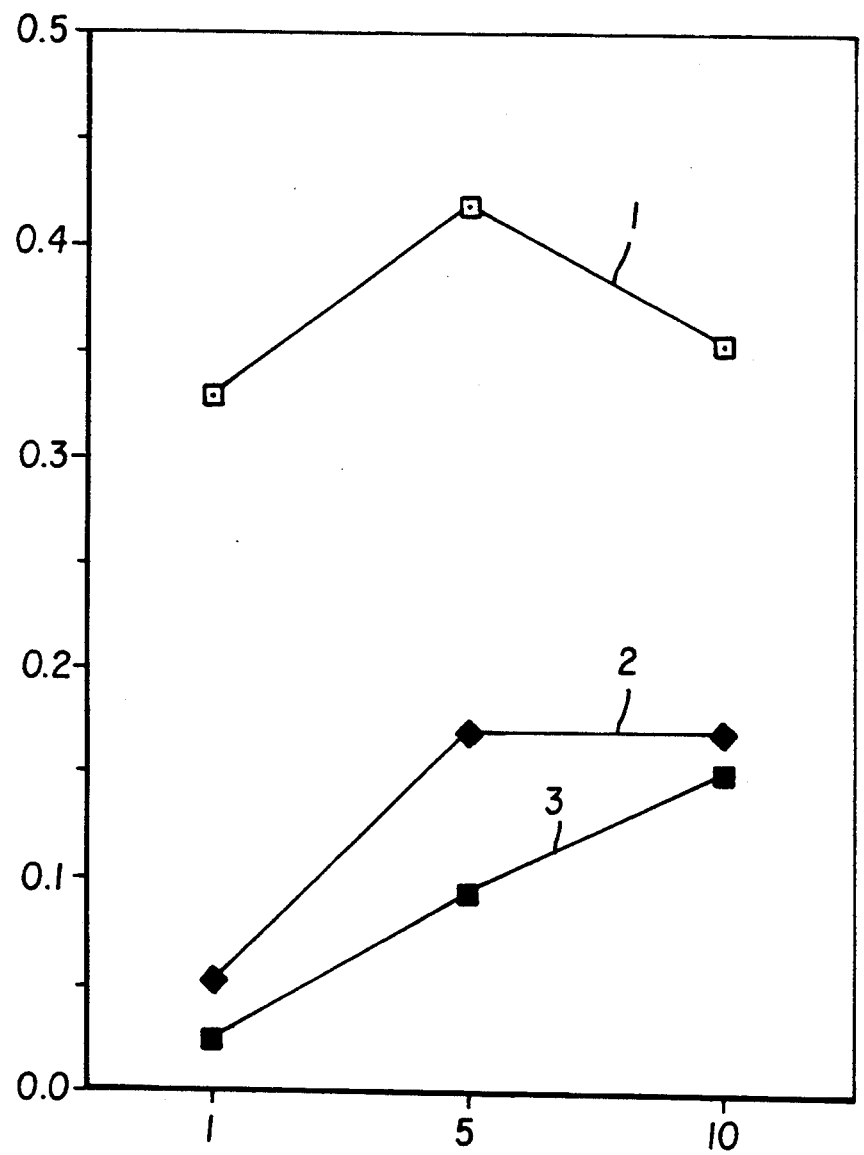
FIG. 8 is a graphical plot of the change in dye signal versus concentration of electron transfer agent for the assays described in Example 10 below.

FIG. 8 shows the data provided by these assays (plotted as rate of change in absorbance of dye signal versus concentration of electron transfer agent, μmolar). In the FIGURE, the invention plot is labeled as "1", and Controls A and B are labeled "2" and "3", respectively. It is apparent that the present invention has greater sensitivity compared to the Control assays over a range of electron transfer agent concentrations.

The invention has been described in detail with particular reference to preferred embodiments thereof, but it will be understood that variations and modifications can be effected within the spirit and scope of the invention. All patents, patent applications (published or unpublished, domestic or foreign), journal literature, books and other published prior art cited herein are incorporated herein by reference for the teaching therein pertinent to this invention.

We claim:

1. An aqueous composition for providing a colorimetric or chemiluminescent signal having a pH of from about 5 to about 10, and comprising:
   a) a colorimetric or chemiluminescent signal generating reagent which provides a signal in response to the catalytic activity of peroxidase, said signal generating reagent being selected from the group consisting of:
      a 2,3-dihydro-1,4-phthalazinedione,
      a tetrazolium salt,
      a diazonium salt, and
      an imidazole or triarylmethane leuco dye, and
   b) an electron transfer agent having structure (I):

structure (I):

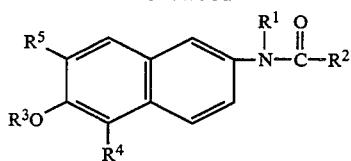

structure (II):

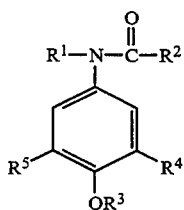

structure (III):

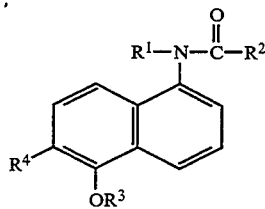

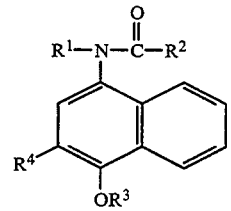

or structure (IV):

wherein $R^1$ is hydrogen or alkyl of 1 to 4 carbon atoms,
$R^2$ is hydrogen or methyl,
$R^3$ is hydrogen or methyl, and
$R^4$ and $R^5$ are independently hydrogen, halo or cyano,
provided that in structure (I), at least one of $R^4$ and $R^5$ is halo cyano.

2. The composition of claim 1 wherein $R^2$ is methyl and both of $R^4$ and $R^5$ are chloro.

3. The composition of claim 1 further comprising a low molecular weight cationic surfactant present at from about 0.05 to about 0.25% above its critical micelle concentration, or from about 0.01 to about 2% of a cationic polymer.

4. The composition of claim 1 further comprising peroxidase or a peroxidase-labeled specific binding molecule.

5. The composition of claim 5 having a pH of from about 5 to about 9 and wherein said signal generating reagent is a triarylimidazole leuco dye to provide a colorimetric signal.

6. The composition of claim 5 further comprising a water-soluble or water-dispersible polymer, the weight ratio of polymer to leuco dye being from about 10,000:1 to about 100:1.

7. The composition of claim 1 further comprising an oxidant for the reaction of peroxidase with said signal generating reagent.

8. The composition of claim 1 having a pH of from about 7 to about 9.5 and wherein said signal generating reagent is a 2,3-dihydro-1,4-phthalazinedione.

9. A diagnostic test kit for the determination of an analyte as the result of the catalytic activity of peroxidase, said kit comprising, in individual packaging:
   i) an aqueous composition for providing a clorimetric or chemiluminescent signal having a pH of from about 5 to about 10, and comprising:
      a) a colorimetric or chemiluminescent signal generating reagent which provides a colorimetric or chemiluminescent signal in response to the catalytic activity of peroxidase, said signal generating reagent being selected from the group consisting of:
         a 2,3-dihydro-1,4-phthalazinedione,
         a tetrazolium salt,
         a diazonium salt, and
         an imidazole or triarylmethane leuco day, and
      b) an electron transfer agent having structure (I):

structure (I):

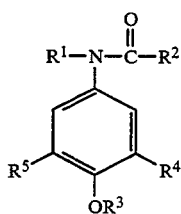

structure (II):

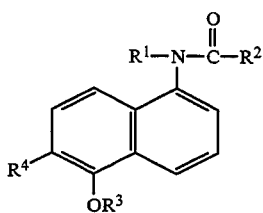

structure (III):

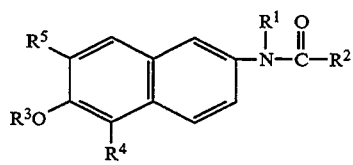

or structure (IV):

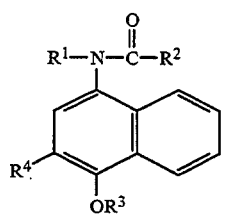

wherein $R^1$ is hydrogen or alkyl of 1 to 4 carbon atoms,
$R^2$ is hydrogen or methyl,
$R^3$ is hydrogen or methyl, and
$R^4$ and $R^5$ are independently hydrogen, halo or cyano,
provided that in structure (I), at least one of $R^4$ and $R^5$ is halo or cyano, and
ii) peroxidase or a peroxidase-labeled specific binding species.

10. The kit of claim 9 further comprising an individually package oxidant for the reduction of peroxidase with said signal generating reagent.

11. A diagnostic test kit for the determination of an analyte as the result of the catalytic activity of peroxidase, said kit comprising, in individual packaging:
   a) a signal generating reagent which provides a colorimetric or chemiluminescent signal in response to the catalytic activity of peroxidase, said signal generating reagent being selected from the group consisting of:
      a 2,3-dihydro-1,4-phthalazinedione,
      a tetrazolium salt,
      a diazonium salt, and
      an imidazole or triarylmethane leuco dye, and
   an electron transfer agent having structure (I):

-continued

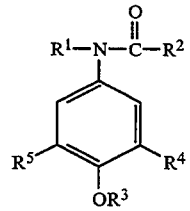

structure (II):

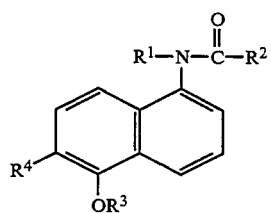

structure (III):

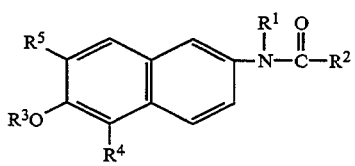

or structure (IV):

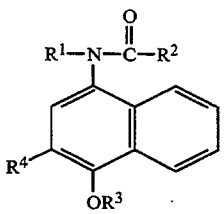

wherein $R^1$ is hydrogen or alkyl of 1 to 4 carbon atoms,
$R^2$ is hydrogen or methyl,
$R^3$ is hydrogen or methyl, and
$R^4$ and $R^5$ are independently hydrogen, halo or cyano,
provided that in structure (I), at least one of $R^4$ and $R^5$ is halo or cyano.

12. A test device for the detection of peroxidase or an analyte catalytically related to peroxidase, said test device comprising an absorbent carrier material, and containing:
   a) a colorimetric or chemiluminescent signal generating reagent which provides a signal in response to the catalytic activity of peroxidase, said signal generating reagent being selected from the group consisting of:
      a 2,3-dihydro-1,4-phthalazinedione,
      a tetrazolium salt,
      a diazonium salt, and
      an imidazole or triarylmethane leuco dye, and
   b) an electron transfer agent having structure (I):

-continued

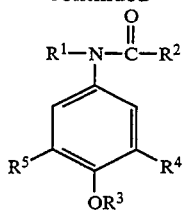

structure (II):

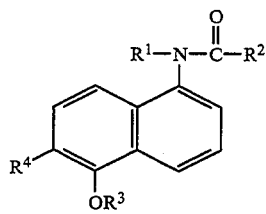

structure (III):

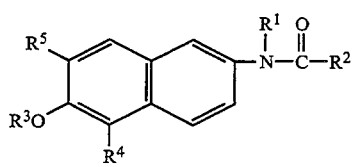

or structure (IV):

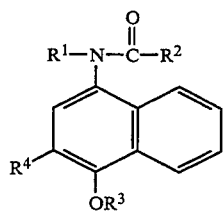

wherein R¹ is hydrogen or alkyl of 1 to 4 carbon atoms,
R² is hydrogen or methyl,
R³ is hydrogen or methyl, and
R⁴ and R⁵ are independently hydrogen, halo or cyano,
provided that in structure (I), at least one of R⁴ and R⁵ is halo or cyano.

13. A method for producing a detectable signal in response to peroxidase comprising:
A. reacting a peroxidase in the presence of
a) a colorimetric or chemiluminescent signal generating reagent being selected from the group consisting of:
a 2,3-dihydro-1,4-phthalazinedione,
a tetrazolium salt,
a diazonium salt, and
an imidazole or triarylmethane leuco dye,
b) an electron transfer agent having structure (I):

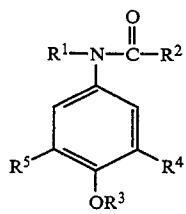

structure (II):

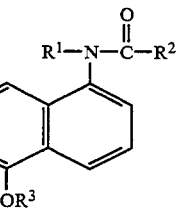

structure (III):

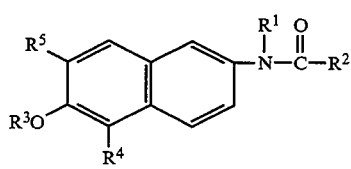

or structure (IV):

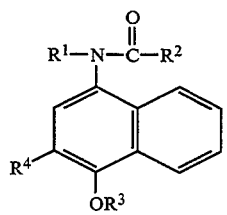

wherein R¹ is hydrogen or alkyl of 1 to 4 carbon atoms,
R¹ is hydrogen or methyl,
R³ is hydrogen or methyl, and
R⁴ and R⁵ are independently hydrogen, halo or cyano,
provided that in structure (I), at least one of R⁴ and R⁵ is halo or cyano, and
c) an oxidant,
to produce a detectable colorimetric or chemiluminescent signal, and
B. determining the resulting colorimetric or chemiluminescent signal as a measure of peroxidase.

14. The method of claim 13 where said peroxidase is present as an analyte or is present in free form for the detection of a non-immunological analyte other than peroxidase.

15. The method of claim 13 wherein said peroxidase is detected as part of a conjugate of peroxidase and a specific binding species.

16. In a specific binding assay for the determination of a specific binding ligand comprising reacting the specific binding ligand with a specific binding partner to form a specific binding complex, and detecting the complex, wherein peroxidase is used as the label to detect the specific binding complex, wherein the improvement comprises contacting the peroxidase-labeled specific binding complex with:
a) a colorimetric or chemiluminescent signal generating reagent selected from the group consisting of:
a 2,3-dihydro-1,4-phthalazinedione,
a tetrazolium salt,
a diazonium salt, and an imidazole or triarylmethane leuco dye,
b) an electron transfer agent having structure (I):

-continued

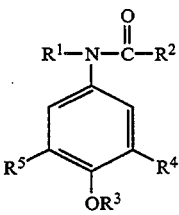

structure (II):

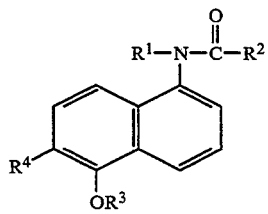

structure (III):

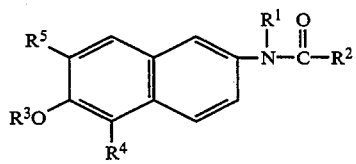

or structure (IV):

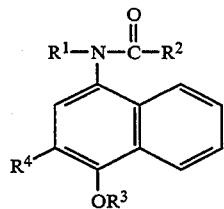

wherein $R^1$ is hydrogen or alkyl of 1 to 4 carbon atoms,
$R^2$ is hydrogen or methyl,
$R^3$ is hydrogen or methyl, and
$R^4$ and $R^5$ are independently hydrogen, halo or cyano, provided that in structure (I), at least one of $R^4$ and $R^5$ is halo or cyano, and
c) an oxidant,
to produce a detectable colorimetric or chemiluminescent signal.

17. The method of claim 16 wherein a second specific binding partner which specifically binds said specific binding ligand is additionally used in order to form a sandwich of specific binding ligand, said specific binding partner and said second specific binding partner, said second specific binding partner being insolubilized or insolubilizable.

18. The method of claim 17 for the determination of an antigen as said specific binding ligand, and wherein said specific binding partner and said second specific binding partner are antibodies specific to said antigen.

19. The method of claim 17 for the determination of a nucleic acid wherein said specific binding partner and said second specific binding partner first and second receptors are oligonucleotides which are complementary to different sequences of said nucleic acid.

20. The method of claim 19 further comprising amplifying said nucleic acid before the reacting step.

21. The method of claim 17 wherein said 2,3-dihydro-1,4-phthalazinedione is luminol, isoluminol, N-(4-aminobutyl)-N-ethylisoluminol hemisuccinimide, N-(6-aminohexyl)-N-ethylisoluminol, N-ethylisoluminol or 7-dimethylaminonaphthalene-1,2dicarboxylic acid,
said imidazole leuco dye is a triarylimidazole leuco dye having the structure (VI):

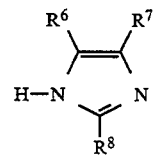

wherein $R^6$, $R^7$ and $R^8$ are independently an organic group such that at least one of them is an o- or p-hydroxy-substituted aryl group of up to 18 carbon atoms in the aromatic ring, and the other two groups being aryl groups chosen such that the imidazole oxidation potential is within the range of from about −70 to about +100 mV as measured by cyclic voltammetry against a standard calomel electrode using a carbon based electrode, and
said oxidant is hydrogen peroxide.

22. The method of claim 17 wherein said compound of structure (I), (II), (III) or (IV) is used in an amount of from about 0.01 to about 10 mmolar, and said signal generating reagent is present in an amount of from about 0.01 to about 10 mmolar.

23. The method of claim 17 wherein the peroxidase-labeled specific binding complex is further complexed with a low molecular weight cationic surfactant present at from about 0.05 to about 0.25% above its critical micelle concentration, or from about 0.01 to about 2% of a cationic polymer.

24. An aqueous composition buffered to a pH of from about 5 to about 10, and comprising:
peroxidase or a peroxidase-labeled specific binding molecule, and
an electron transfer agent having structure (I):

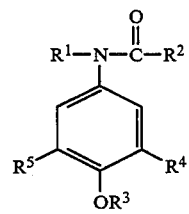

structure (II):

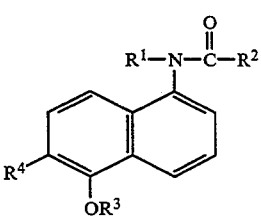

structure (III):

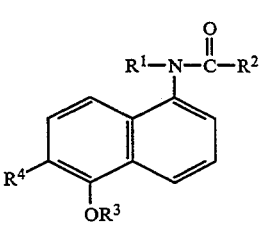

-continued
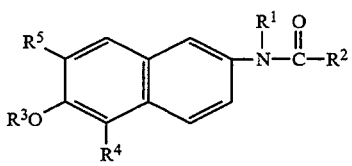
or structure (IV):
-continued
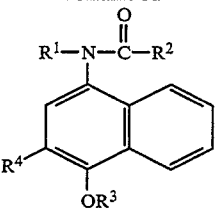
wherein $R^1$ is hydrogen or alkyl of 1 to 4 carbon atoms,
$R^2$ is hydrogen or methyl,
$R^3$ is hydrogen or methyl, and
$R^4$ and $R^5$ are independently hydrogen, halo or cyano,
provided that in structure (I), at least one of $R^4$ and $R^5$ is halo or cyano.
* * * * *